United States Patent [19]

Lee

[11] Patent Number: 4,909,737

[45] Date of Patent: Mar. 20, 1990

[54] DENTAL APPARATUS

[76] Inventor: Robert L. Lee, 22575 Barton Rd. Grand Terrace, Colton, Calif. 92324

[21] Appl. No.: 200,635

[22] Filed: May 27, 1988

[51] Int. Cl.⁴ .............................................. A61C 19/04
[52] U.S. Cl. .......................................... 433/73; 433/69
[58] Field of Search .................................... 433/69, 73

[56] References Cited

U.S. PATENT DOCUMENTS

| Re. 31,615 | 6/1984 | Lee | 433/73 |
|---|---|---|---|
| 1,705,223 | 3/1929 | McLean | 433/69 |
| 3,035,348 | 5/1962 | Page | 433/69 |
| 3,056,210 | 10/1962 | DePietro | 33/514 |
| 3,078,584 | 2/1963 | Cohn | 33/514 |
| 3,490,146 | 1/1970 | Guichet | 433/69 |
| 4,561,846 | 12/1985 | Polizzotto | 433/73 |

OTHER PUBLICATIONS

A Sheet Showing Figure 26 From a Publication by the Panadent Corporation.

Primary Examiner—Robert Peshock
Attorney, Agent, or Firm—Knobbe, Martens, Olson & Bear

[57] ABSTRACT

Upper and lower frames of jaw movement analyzing apparatus is disclosed. A segmented clamp interconnects the side arms of the lower frame to a forward transverse rod in a manner to simplify locating the jaw hinge axis. The clamp includes a screw for gripping the rod with two of the clamp segments for maintaining the arms in adjusted angular positions while permitting further easy adjustment. The clamp also includes separate ball screws engaging a side arm to maintain axial positioning of the arm and permitting further easy adjustment. A lock screw extends through the clamp segments to lock the arms in the located hinge axis position.

12 Claims, 2 Drawing Sheets

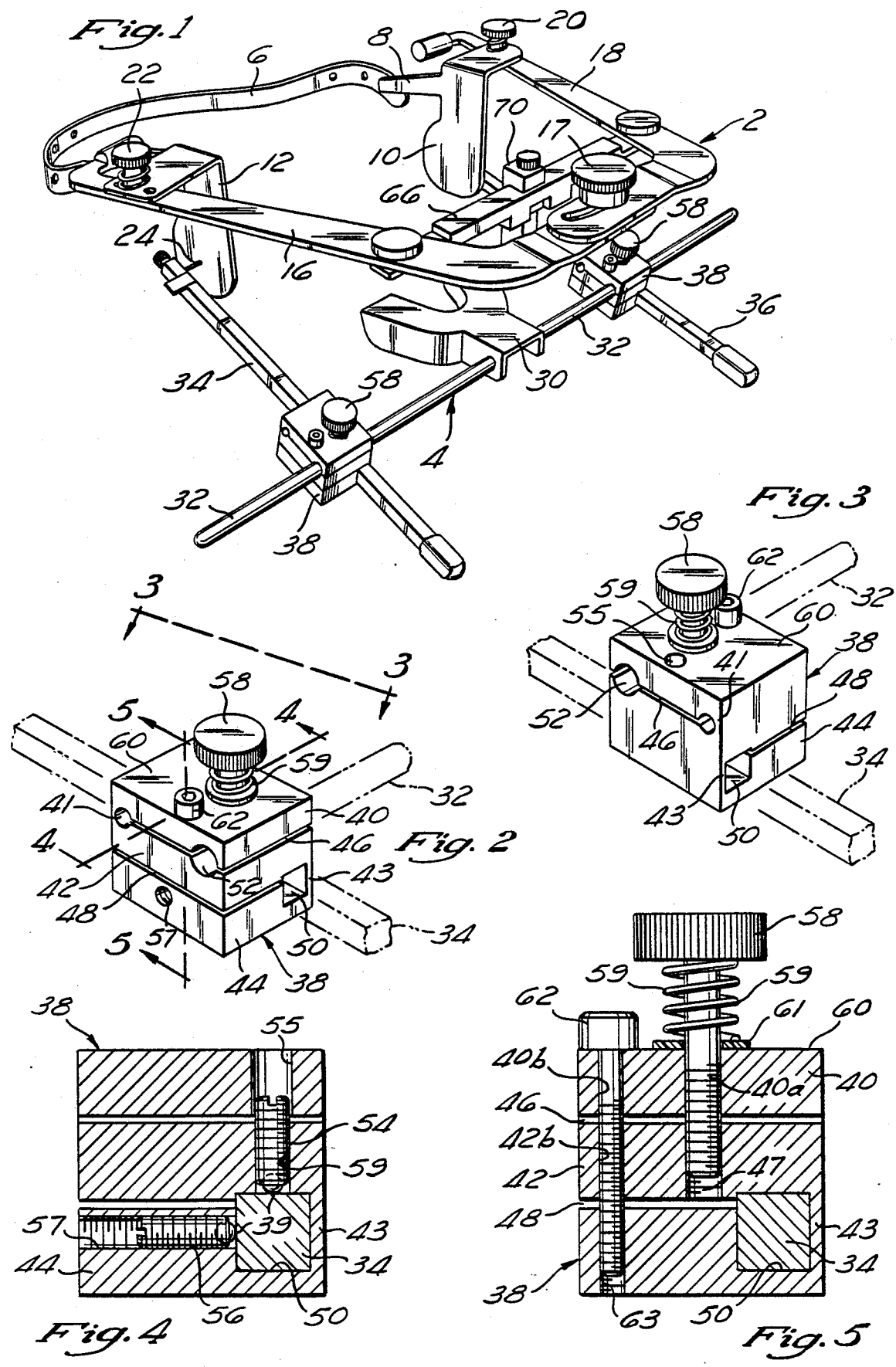

DENTAL APPARATUS

BACKGROUND OF THE INVENTION

1. Field of the Invention

The present invention relates to improvements in apparatus for recording or analyzing jaw movements.

2. Description of the Prior Art

In analyzing and treating jaw disorders and in making dental prosthesis, it is desirable to simulate the individual patient's jaw movements. To do this on a dental articulator, it is first necessary to analyze the jaw movements and it is desirable that the apparatus be available to quickly and accurately perform such functions.

One system for analyzing jaw movements is set forth in U.S. Pat. No. RE 31,615 to Robert L. Lee, wherein an upper frame or face bow is mounted on a patient's nose and ears with side arms supporting rigid recording plates overlying the patient's temporomandibular joints. A grid of intersecting lines on graph paper is provided on the recording plates. A lower or mandibular frame is mounted by means of a dental clutch to the patient's lower jaw so as to move with the jaw. Side arms of the lower frame carry writing elements for tracing on the graphs jaw movements.

In use of such apparatus, it is usually initially necessary to locate the hinge axis about which the lower jaw rotates when it is in its rearward most position and moved in mouth closing and opening directions. The writing element will trace an arc on the graph paper unless the element is on the hinge axis. If the element remains stationary, making a single point on the graph paper, the hinge axis of the patient's jaw has been located. Normally as initially mounted, the writing element or stylus carrying the element is not on the hinge axis and hence it is necessary to make suitable adjustments to move the stylus so that it is on the axis. Typically, the lower head frame has two parallel side arms mounted by suitable clamps to a forward transverse rod, which is perpendicular to the side arms. In the aforementioned patent, the front-to-rear location of the stylus is varied by rotating an adjustment screw which changes the length of the side arm in relation to its attachment point on the transverse rod. The vertical location of the stylus is changed by way of a second adjustment screw which moves the side arm in an arc about the transverse rod. While this approach is capable of making precise incremental adjustments in the location of the stylus, it takes considerable time and skill to move the side arm so that the stylus is aligned with the hinge axis. After an adjustment is made, it is necessary to hinge the jaw to see whether an arc is being made by the stylus or whether it is on the axis. Typically, an adjustment will be made which moves to the other side of the axis, and it is necessary to make further smaller adjustments until the proper location is reached. Frequently, new operators will make mistakes in this process such as rotating an adjustment screw in the wrong direction. U.S. Pat. No. 3,035,348-Page also shows a system employing adjustment screws for locating the hinge axis wherein considerable time and skill is required.

Another known, simpler system employs a clamp connecting the side arms of a lower frame to the forward transverse rod wherein the side arm is slidable front-to-rear in the clamp and is rotatable with the clamp about the transverse rod. A clamping screw holds the side arm in a selected front to rear and rotational position. While such a system is simple in construction, it does not work very well because loosening the clamping screw permits the arm to fall or move in both of its adjustment directions, and it is difficult to make both the angular and the front-to-rear adjustments at one time and then tighten the clamp screw to hold the arm in the selected position. If the selected position is incorrect, it is necessary to unloosen the clamping screw, and the prior position that might have been fairly close to being correct is often lost such that the process must be repeated several times before proper adjustment is made.

It is, therefore, desireable to have a mounting arrangement which will permit the practitioner to readily adjust the arcuate position and the front-to-rear position of a side arm in a minimum amount of time. Further, it is desirable that the apparatus be capable of independent adjustment of the position of each side arm.

SUMMARY OF THE INVENTION

Briefly stated, the invention provides a frame to be mounted on the patient's lower jaw by means of a clutch attached to the lower teeth or gums, with a transverse rod attached to the clutch and a pair of side arms, each being connected to the rod by a clamp. A stylus extends inwardly from the rear portion of each side arm to engage a recording plate which overlies the patient's temporomandibular joint. Each side arm is independently slidable forwardly and rearwardly in its clamp. A friction-producing means within the clamp permits relatively easy movement of the side arm within the clamp, but yet maintains the arm fairly in a selected position; thereby permitting quick and easy front-to-rear adjustment of the stylus. The clamp together with the side arm is rotatable about the transverse rod to cause the stylus on the rear of the side arm to move vertically in an arcuate path. Friction-producing means between the clamp and the rod permit the clamp and the arm to be rotated relatively easily, but yet provide sufficient friction to maintain the clamp and the side arm in a selected position, thus making vertical movement of the stylus relatively quick and easy. Once the stylus is in a desired position, a clamping screw or other such means is actuated to lock the clamp so that the side arm is locked in a selected position.

In a preferred form of the invention, the clamp is a block-like member formed of three stacked segments which include portions which are spaced from the adjacent segment, except that an upper and a center segment are joined at one edge by an integral hinge section, and the lower and center segment are similarly joined at one edge. With this arrangement, the spaced portions of the segments can be moved towards each other to provide a clamping action. The side arm extends through an aperture formed by two of the segments. Friction-producing means mounted in one or more of these two segments engage the side arm in a manner to permit it to be moved relatively easily, but will keep the arm in a selected position unless positively moved. A second aperture is formed in the spaced portions of the middle segment and the third segment, and a screw is provided to clamp those two segments together to provide sufficient friction on the transverse rod that permits the clamp in the side arm to be rotated about the rod, but will hold the clamp in a selected position. A locking screw extends into all three segments in a manner to merge the spaced portions more tightly together so as to grip the side arm and the transverse rod tightly and lock the side arm in a selected position.

BRIEF DESCRIPTION OF THE DRAWINGS

FIG. 1 is a perspective view illustrating upper and lower frames of jaw movement analyzing equipment incorporating the invention;

FIG. 2 is an enlarged perspective view of the clamp of the invention with a side arm and the transverse rod of the frame of FIG. 1 being shown in phantom;

FIG. 3 is an enlarged perspective view of the clamp on Line 3—3 of FIG. 2;

FIG. 4 is a cross-sectional view of the clamp on Line 4—4 of FIG. 2;

FIG. 5 is a cross-sectional view of the clamp on Line 5—5 of FIG. 2;

DETAILED DESCRIPTION OF THE PREFERRED EMBODIMENT

Figure 6:
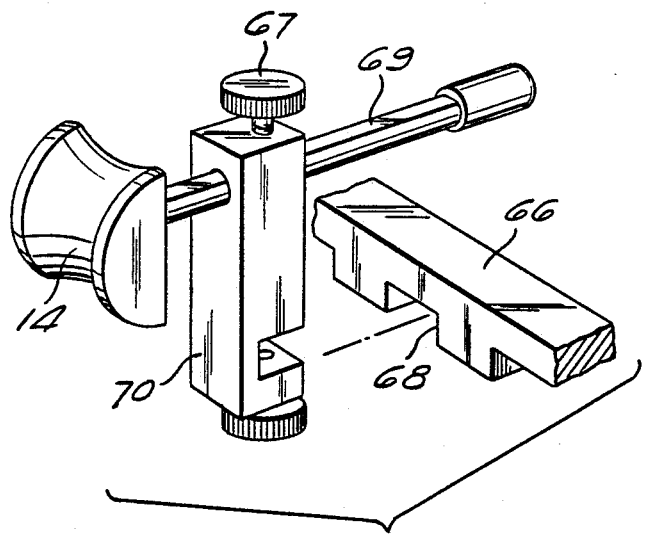
FIG. 6 is an exploded perspective view of the upper frame nasion relator and its mounting structure.

Referring to FIG. 1, there is illustrated an upper head frame or face bow 2 cooperating with a lower mandibular frame 4 of jaw movement analyzing apparatus. As can be seen, the face bow 2 has a generally U-shaped configuration formed of two generally horizontally flat segments forming side arms 16 and 18 having forward portions adjustably joined by a screw 17 that extends through slots in the forward portions of the side arms. A strut 66 extends horizontally with one end pivotally secured to side arm 16 and the other end pivotally secured to side arm 18. The central portion of the strut 66 is formed with a slot 68, as best seen in FIG. 6. A vertically oriented bracket 70 includes a slotted portion which mates with the slot 68 so as to mount the bracket on the strut 66. A suitable set screw is provided to hold the bracket in position. A nasion relator 14 (FIG. 7) is mounted on a pin 69 that extends horizontally through one end of bracket 70. A set screw 67 is provided to hold the pin 69 in a selected position.

A pair of recording plates 10 and 12 are respectively secured to the rear portions of the side arms 16 and 18. Each recording plate includes a horizontal portion respectively secured by screws 20 and 22 to the arm 16 and 18, and depending vertical portions which form the writing surfaces. The recording plates 12 and 14 further each include a rearwardly extending arm 8 to which is attached a flexible strap 6. The nasion relator 14 is contoured to fit against the bridge of the patient's nose. The arms 8 of the recording plates are adapted to extend above and be supported on the ears while the strap 6 is worn behind the patient's head.

Figure 8:
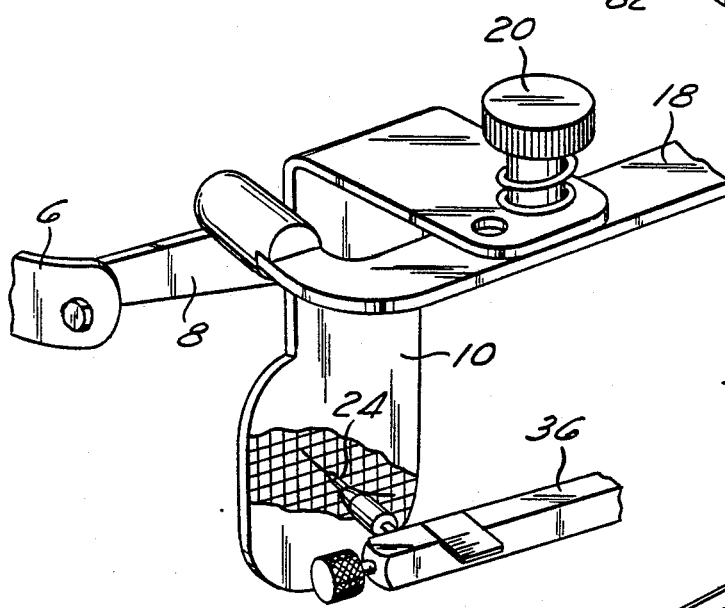
FIG. 8 in an enlarged perspective view of one of the recording points of the upper frame together with the stylus portion of the lower frame of FIG. 1.
Figure 9:
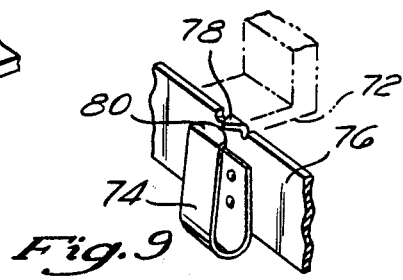
FIG. 9 in an enlarged perspective view of a mounting clip on a reference tool, with a portion of the upper frame structure forming a reference point to cooperate with the reference tool.

The vertical portions of the recording plates 12 and 14 are positioned in front of the patient's ear, and extend over the temporomandibular joints when the face bow is mounted on the patient's face. As shown in FIG. 8, the outer surface of each plate is a grid of vertical/horizontal intersecting lines. The grid may conveniently be formed on a separate sheet of paper held by adhesive to the plate such that the sheet is readily removable from the recording plate for storing patient data.

The mandibular frame 4 includes a clutch 30 adapted to be mounted by plaster to the patient's lower teeth or gums. A transverse rod 32 of circular cross-section extends through the forward portion of the clutch 30. Elongated side arms 34 and 36 are adjustably connected to the transverse rod 32 by a pair of clamps 38. The side arms are rigid and preferably formed with square cross-section as indicated.

Positioned on the rear portion of each of the side arms 34 and 36 is a stylus 24 which extends inwardly towards an adjacent recording plate when the apparatus is mounted on a patient. A suitable lead or other writing element is mounted in the stylus for marking the graph paper on the recording plate.

Referring now to FIGS. 2-5, the clamps 38 are uniquely constructed to provide for quick and accurate adjustment of the side arms. As seen, the clamps have a generally cube shape, and in the orientation illustrated, are formed with three stacked segments. This includes upper segment 40 and middle segment 42 and a bottom segment 44. The rear edges of the segments 40 and 42 are formed integral with each other by a hinge section 41 while the remaining portions of the segments 40 and 42 are separated by a slot or space 46 which extends horizontally forwardly from the hinge section 41 completely to the front edge of the segments 40 and 42. Also, the space 46 extends completely from one side of the segments 40 and 42 to the other side. The clamp is preferably made of strong but somewhat springy, and preferably light metal, such as aluminum. The hinge section 41 is dimensioned such that spaced portions of the segments 40 and 42 can be urged towards each other so that they in effect form jaws of a clamp that pivot slightly about the hinge 41. The rearward portion of space 46 is enlarged into a circular bore as a means to adjust the strength of the hinge 41, thereby adjusting the sensitivity of the clamp formed by the jaws 40 and 42. These jaws will return to the position illustrated in the drawings when unstressed. A rod clamping screw 58 is provided to urge these jaws together as desired. The lower end of the clamping screw 58 extends through an unthreaded 40a hole in the upper segment 40 and threads into a threaded hole 47 in the central segment 42. A compression spring 59 extends between the head of the screw 58 and a washer 61, which engages the upper surface 60 of the segment 40 around the shank of the screw 58.

As best seen from FIGS. 2 and 3, an elongated cylindrical aperture 52 extends horizontally through forward portions of the segments 40 and 42. That is, a portion of the hole is formed in the lower surface of the segment 40 and a mating portion is formed in the upper surface of the segment 42. The aperture which extends completely through the clamp from one side to the other, is sized and shaped to receive the transverse rod 32.

The lower surface of the center segment 42 is spaced from the upper surface of the lower segment 44 by a space or slot 48 with the slot extending through the entire clamp except for a hinge segment 43 along one edge of segments 42 and 44. The hinge section 43 extends from the forward face of the clamp to its rearward face on one side of the clamp. The remaining portions of the facing surfaces of the segments 42 and 44 are spaced from each other by the slot 48.

An elongated aperture 50, having a square cross-section, extends through the clamp from the front surface to the rear surface and is sized and shaped to slidably receive a side arm 34 or 36. The aperture 50 is mainly located within the lower segment 44, but a portion of the aperture 50 also extends into the lower surface of the center segment 42. To provide friction against movement of the side arm 34 relative to the clamp 38, so as to facilitate accurate adjustment there is provided a pair of set screws 54 and 56 which engage two different faces of the side arm at right angles to each other, as best seen in FIG. 4. The set screw 54 is inserted through a hole 55 in the upper segment 40 without any interference, and threads into a threaded hole 59 in the center segment 42. The set screw 56 extends horizontally, having been threaded into a tapped hole 57 in the lower clamp segment 44. Each of the set screw friction generated includes a ball 39 on its tip which is biased axially outwardly by a spring captured within the set screw. The set screws 54 and 56 are known components often referred to as ball screws. They are advantageous for providing fine adjustment to the amount of rolling friction applied to an element, such as the side arm 34, and do not mark the arm.

A locking screw 62 extends through an unthreaded hole 40b in the upper segment 40 and an unthreaded hole 426 in the center segment 42 and threads into a threaded hole 63 in the lower segment 44 as seen there holes are located along one edge of the clamp transversely spaced from the hinge section 43 and forwardly spaced from the hinge section 41. A locking screw 62 is positioned on the holes and threaded tightly into the hole 63, the head of the locking screw draws the upper segment 40 towards the center segment 42 and the threaded end of the locking screw draws the lower segment 44 towards the center segment 42.

In operation, the upper frame 2 is mounted on a patient's nose and ears as indicated above and the lower frame 4 is clutched to the teeth so that the lower frame moves with the mandible. With the frames roughly positioned as shown in FIG. 1, the styluses overlie the recording plates, but they are to be aligned with the patient's hinge axis. To accomplish this, the patient's mandible is moved rearwardly to its fully retruded position, and the mandible is then hinged in a mouth closing and opening operation. Unless the stylus happen to be exactly on the hinge axis, it will move in an arcuate path, spaced somewhat from the hinge axis to be located. If the curve formed has its concave side facing forwardly, this tells the operator that the hinge axis is forward of that curve. Thus, the operator would slide the side arm 34 forwardly and move the jaw again in a hinging action. If this makes a curve with the concave side facing rearwardly, this tells the operator that the hinge axis is somewhere between those two curves. The set screws 54 and 56 are adjusted in a manner to produce desired amount of friction on the side arm 34. This desired amount will permit the side arm to be moved readily with moderate finger force, but is sufficient such that it is unlikely to be inadvertently or unintentionally moved. This friction on the side arm allows the forward and rearward adjustment of the side arm to be readily made so that the jaw can be hinged quickly into several adjusting positions until the stylus 24 moves in a single curve. This tells the operator that the hinge axis is on that curve.

It is also necessary to move the rear portion of the side arm 34 upwardly or downwardly until the stylus stops moving during hinging action of the mandible. This tells the operator that the hinge axis has been located. The up and down movement of the rear portion of the side arm is accommodated by the aperture 52 in the clamp being in slidable engagement with the transverse rod 32. The semi-cylindrical sections of the aperture 52 that extend completely across the clamp provide a large surface area of the clamp in contact with the rod 32. Tightening the screw 58 through the spring 59 draws the jaws 40 and 42 more tightly against the rod 32 to increase the friction while loosening the screw decreases the friction. It is easy to adjust the screw to provide the desired amount of friction that will permit the side arm 34 together with the clamp to be rotated around the rod 32, but yet will cause the side arm to remain in a selected position when released, as opposed to slipping inadvertently to some other position. Thus, again it is easy to quickly move the side arm to the desired position.

Once the hinge axis has been located, the locking screw 62 is threaded tightly into the tapped hole 63 so that the upper segment 40 is drawn tightly against the first rod 32, locking the clamp and hence the arm 34 to prevent further rotation of the clamp about the rod. Simultaneously, the lower segment 44 is drawn towards the center segment 42 to provide clamping action on the side arm 34, thus locking the side arm from forward or rearward movement.

This same procedure is then followed for the side arm 36 to locate the hinge point on that side. The location of these two points on each side establishes the hinge axis. With the second clamp then locked in position, the frame 4 is thus rigidly secured to the patient's mandible so that further jaw movements may be traced on fresh graph paper applied to the recording plate.

FIG. 8 illustrates the mandible having been moved through a certain path such as a protrusive path, making the curve indicated on the graph. Similarly, the mandible is normally moved into right and left side-shift positions that include forward movement as well, such that a different type of curve is formed. This action is explained in greater detail in the above identified Lee Patent.

Figure 7:
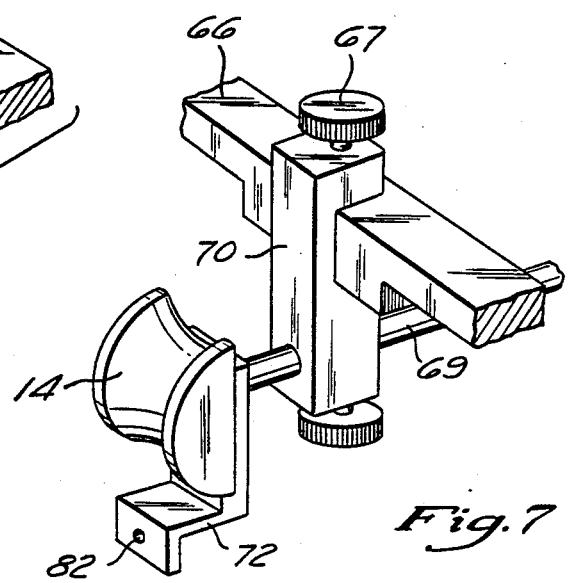
FIG. 7 is a perspective view of the nasion relator of FIG. 6 connected to its mounting structure in a position inverted of that of FIG. 6.
Figure 10:
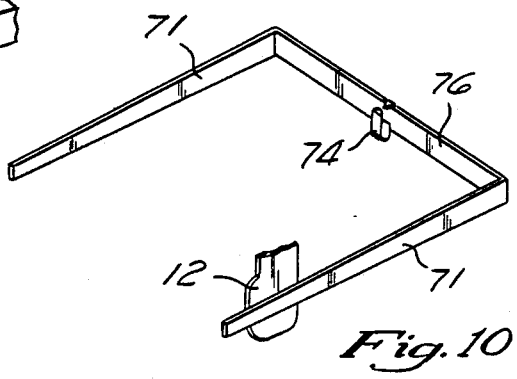
FIG. 10 is a perspective view of a reference plane tool.

Once the desired tracings have been made, the upper frame can be readily removed from the patient. Before removing the tracings from the recording plates, it is desirable to form a reference line on the graph papers. For this purpose there is provided a reference plane tool 76 illustrated in FIG. 10. This tool is a somewhat flexible, but yet vertically rigid member having a forward portion and a pair of side arms 68. The reference tool 76 is sized to fit onto the upper frame 2 with the side arm 68 extending adjacent to the recording plates as illustrated in FIG. 10. The forward portion of the reference tool is provided with a spring clip 74 having a pointed tab 80 which is aligned with a pointed protrusion 78 on the central portion of the transverse arm 76 of the reference tool. Protrusion 78 and the tab 80 fit within conical recesses 82 formed in a vertically extending portion of the mounting bracket 72, as seen in FIG. 7, slidably mounted on pin 69. The bracket 72 is secured by a suitable set screw (not shown), in the position illustrated in FIG. 7, such that the reference tool can be attached to the bracket.

With the reference tool secured at its forward end to the reference pointer socket 82 and with the upper edges of the side arm 68 passing through the hinge axis which has been located on each of the graph papers on each side of the upper frame, three points have been established, and these three points define a reference plane. The upper edge of the reference plane tool is in this plane. Thus, a line is drawn on the upper edge of the side arm of the reference tool on each of the recording plates. This action accurately establishes a reference line on each of the graph papers. By using this reference line, the angle of the curved paths on the graphs can be measured and such measurement information is utilized to set a dental articulator to accurately simulate the patient's jaw movements. Such use of that information is well known and described in the above referenced Lee Patent.

With the bracket 70 positioned as shown in FIG. 6, the upper face bow interferes with the proper positioning of the reference plane tool. However, with the vertical bracket 72 can be inverted, as shown in FIG. 7, so that the reference plane mounting tool bracket 72 can be located below the nasion relator 14 and below the lower end of the bracket 70. This enables the reference tool to be easily mounted on the bracket 72. The upper face bow can be used with the bracket as shown in FIG. 6, if the reference tool is not to be used.

What is claimed:

1. Apparatus for analyzing jaw movement including a frame to be attached to a patient's mandible, said frame comprising:
   a transverse rod to be connected by a clutch to a patient's mandible and to extend horizontally, spaced closely in front of a patient's face;
   a side arm extending generally perpendicular to the rod to be positioned adjacent to the side of a patient's face extending towards the patient's ear;
   a clamp slidably mounted on said rod and slidably receiving said side arm for connecting the side arm to the rod, said clamp being constructed to permit the side arm to be slidably moved axially forwardly and rearwardly, and to permit the side arm to be rotated about said rod, said clamp including a side arm friction generator applying friction to said side arm that will permit the side arm to be moved axially, but will cause the side arm to remain where axially positioned unless positively moved, said side arm friction generator applying friction to the side arm without interfering with the rotational movement of the side arm and the clamp about said rod, said clamp further including a rod friction generator which applies friction between the clamp and the rod that permits the side arm and the clamp to be rotated relative to the rod, but causes the side arm and the clamp to remain in a selected rotational position unless positively moved, said rod friction generator not interfering with the axial movement of said side arm.

2. The apparatus of claim 1, wherein said friction generators include adjustable structure that permits the amount of friction generated by each of the generators be adjusted as desired.

3. The apparatus of claim 1, wherein said clamp includes a lock for locking the side arm, the clamp and the rod in a selected position.

4. The apparatus of claim 3, wherein said lock is operable independently of the friction generators.

5. The apparatus of claim 1, wherein said clamp includes a pair of jaw-like segments, including major portions that are spaced from each other that are formed to engage said rod, said segments being joined by an integral hinge section, and a rod clamping screw urging said jaw-like segments towards each other to grip said rod to provide a desired amount of friction on the rod.

6. The apparatus of claim 1, wherein said clamp includes a pair of jaw-like segments with major portions closely spaced from each other formed to engage said side arms, and having a hinge section integrally joining said segments in a manner that permits said jaw-like segments to be urged towards each other to provide a gripping action.

7. The apparatus of claim 6, wherein said clamp includes a lock for clamping said jaw segments tightly onto said side arm and said rod to lock the arm in a selected position with respect to said clamp and rod.

8. The apparatus in claim wherein said arm friction generator includes a ball screw threaded into said clamp to engage said arm to produce a desired amount of friction.

9. The apparatus of claim 1, wherein said clamp has a generally block-like configuration formed in three stacked segments which extend across the block and include major portions which are spaced from each other, one of the outer segments being integrally hinged to a central segment along one edge of said one segment and said center segment in a manner such that the spaced portions of said one segment and said center segment can be urged towards each other to provide a clamping action, said one segment and said center segment having an elongated cylindrical aperture formed within the facing surfaces of said one segment and said center segment, said cylindrical aperture being adapted to receive said rod, an adjustment screw extending through said one segment and threading into said center segment to urge said first pair of segments towards each other to grip said rod with a desired amount of friction thereby forming said rod friction generator;
   the other one of said outer segments and said center segment being joined by an integral hinge section along one edge of said other segment and said center segment, said second hinge section being perpendicular with respect to said first hinge section, said second pair of segments having an elongated aperture formed therein adapted to slidably receive said side arm, said side arm friction generator including ball screw means threaded into said clamp to engage said arm to provide a desired amount of friction; and
   an elongated lock screw extending through said clamp perpendicular to the spaces between said segments, said lock screw having an elongated shank which extends through said one outer segment and said center segment in unrestricted fashion and threads into the other outer segment, whereby said segments may be drawn towards each other by the thread connection between the lock screw and said one outer segment and a head on said screw engaging said one outer segment, whereby said segments grip said arm and said rod to lock them in a desired selected position.

10. An apparatus for locating a patients jaw hinge axis comprising:
   a pair of side arms;
   a transverse rod extending perpendicular to the side arm;
   a clamp connecting a side arm to said transverse rod, the clamp slidably receiving the rod for rotation of the clamp relative to the rod, and the clamp slidably receives said arm in a manner to permit axial movement of the arm in the clamp;

means on said clamp for adjusting the amount of friction on said side arm;

means on said clamp for adjusting the amount of friction on said transverse rod; independent of said arm friction means; and means on said clamp for simultaneously locking the clamp on said rod and said arm in a selected position.

11. A clamp comprising a block formed in three stacked segments which extend across the block and include major portions which are spaced from each other, one of the outer segments being integrally hinged to a central segment along one edge of said one segment and said center segment in a manner such that the spaced portions of said one segment and said center segment can be urged towards each other to provide a clamping action, said one segment and said center segment having an elongated cylindrical aperture formed within the facing surfaces of said one segment and said center segment, said cylindrical aperture being adapted to receive a rod;

an adjustment screw extending through said one segment and threading into said center segment to urge said outer segment and said center segment towards each other to grip said rod with a desired amount of friction;

the other one of said outer segments and said center segment being joined by an integral hinge section along one edge of said other segment and said center segment, said hinge section being perpendicular with respect to the the first mentioned hinged section, said outer segment and said center segment having an elongated aperture formed therein adapted to slidably receive an elongated element, means threaded into said clamp to engage said element to provide a desired amount of friction on it; and an elongated lock screw extending through said clamp segments, said lock screw having an elongated shank which extends through said one outer segments and said center segment in unrestricted fashion and threads into the other outer segment, whereby said outer segments may be drawn towards each other by the threaded connection between the lock screw and said one outer segment and a head on said screw engaging said one outer segment, whereby said segments grip said element and said rod to lock them in a desired selected position.

12. A method of axially and rotationally positioning an elongated side arm with respect to a transverse rod of a lower frame to be attached to the mandible of a patient to analyze jaw movements comprising:

mounting a segmented clamp on said rod with the clamp having an elongated aperture for receiving the rod;

inserting said side arm through an elongated aperture in said clamp in an orientation perpendicular to said rod;

rotating said clamp and said arm about said rod to a desired angular orientation;

gripping the rod with sufficient force to maintain the clamp and the arm in a selected rotational position, while permitting the arm and the clamp to be rotated relatively easily;

engaging said side arm independently of the gripping of said rod, with a force sufficient to cause said side arm to remain in a selected axially moveable position within said clamp while permitting the side arm to be moved axially relatively easily, overcoming the friction generated between the clamp and the side arm; and locking segments of said clamp in a manner to apply friction between the clamp and the rod and between the clamp and the arm sufficient to prevent movement between the clamp and the rod and the clamp and the arm, thereby holding the rod, clamp and arm in a selected position.

* * * * *